United States Patent [19]

Stünkel et al.

[11] Patent Number: 4,737,521
[45] Date of Patent: Apr. 12, 1988

[54] SURAMIN SODIUM FOR USE AS AN IMMUNOSTIMULANT

[75] Inventors: Klaus G. Stünkel, Wuppertal; Rudi Grützmann, Solingen, both of Fed. Rep. of Germany

[73] Assignee: Bayer Aktiengesellschaft, Leverkusen, Fed. Rep. of Germany

[21] Appl. No.: 867,865

[22] Filed: May 27, 1986

[30] Foreign Application Priority Data

Jun. 11, 1985 [DE] Fed. Rep. of Germany ........ 3520846

[51] Int. Cl.$^4$ ............................................ A61K 31/185
[52] U.S. Cl. ........................................ 514/577; 514/885
[58] Field of Search .............................. 514/577, 885

[56] References Cited

PUBLICATIONS

Chemical Abstracts, 93: 93395r (Fletcher et al.), 1980.
The Merck Index, 9th Ed., 1976, p. 8796.
Ivan M. Roitt, "Essential Immunology", 5th Ed., pp. 238–239.
O. G. Bier et al., "Fundamentals of Immunology", pp. 260–261.

Primary Examiner—Leonard Schenkman
Attorney, Agent, or Firm—Sprung Horn Kramer & Woods

[57] ABSTRACT

A method of stimulating the immune response of a patient which comprises administering to a patient in need thereof an immunostimulating effective amount of 8,8'-[carbonylbis]imino-3,1-phenylenecarbonylimino(4-methyl-3,1-phenylene)carbonylimino]]bis-1,3,5-naphthalenetrisulphonic acid hexasodium salt.

1 Claim, No Drawings

SURAMIN SODIUM FOR USE AS AN IMMUNOSTIMULANT

The invention relates to suramin sodium for use as an immunostimulant, to immunostimulant medicaments containing suramin sodium, and to a process for the preparation of such medicaments.

According to the Merck Index, 10th Edition, No. 8890, suramin sodium corresponds to the chemical compound 8,8'-[carbonylbis[imino-3,1-phenylenecarbonylimino(4-methyl-3,1-phenylene)carbonylimino]]-bis 1,3,5-naphthalenetrisulphonic acid hexasodium salt, and has hitherto been used with success against trypanosomes and filariae.

Suramin sodium and its preparation belong to the known state of the art. Literature which deal with suramin sodium and which may be mentioned by way of example include: Fourneau et al., Compt. Rend, 178, 675 (1924); British Patent Specification No. 224,849; Heymann, Angewandte Chemie 37 585 (1924); Olenick, Antibiotics Vol. 3; J. W. Corcoran, F. E. Hahn, Eds. (Springer Verlag, New York, 1975) pages 699-703.

It has now been found that the known suramin sodium has an immunostimulant action.

The invention relates to 8,8'-[carbonylbis[imino-3,1-phenylenecarbonylimino(4-methyl-3,1-phenylene)carbonylimino]]bis 1,3,5-naphthalenetrisulphonic acid hexasodium salt (=suramin sodium according to the Merck Index, 10th Edition, No. 8890) for use as an immunostimulant for the therapeutic treatment of the human or animal body.

The invention also relates to medicaments containing suramin sodium as an immunostimulant, for the therapeutic treatment of the human or animal body.

The invention also relates to the use of suramin sodium as an immunostimulant and for the elimination of immune deficiencies of the human or animal body, to the use of suramin sodium for the preparation of immunostimulant medicaments, and to a process for the preparation of immunostimulant medicaments in which suramin sodium according to the definition in claim 1 is mixed with inert, non-toxic, pharmaceutically suitable excipient.

Suramin sodium exhibits a pronounced resistance-increasing action. It has emerged that suramin sodium increases, in an antigen-specific manner, the antibody synthesis of the immune system, and increases the proliferation of T-lymphocytes. These results were obtained using the experimental design which follows.

Increase in the primary humoral immunity in vitro to sheep erythrocytes (SE).

It is possible experimentally to induce the development of a humoral immune response with heterologous red blood cells by primary immunization of mouse spleen cells in suspension cultures in vitro (R. I. Mishell and R. W. Dutton, J. Exp. Med. 126, 423 (1967)).

For this purpose, Balb/c mouse spleen cells are cultivated in the presence of antigen (SE) and the test substance for 5 days. The cells are harvested, washed and plated out together with the antigen and complement in semisolid agar, and incubated at 37° C. for 2 hours (N. K. Jerne, A. A. Nordin and C. Henry, "Cell bound Antibodies", eds. Amos and Koprowski, Wistar Inst. Press, Philadelphia, USA, page 109 (1963)). The antigen sensitization of mouse lymphocytes in the primary culture results in the synthesis and release of antibodies. The specific antibodies which are secreted bind to the SE antigen and lyse these cells due to the presence of complement (plaque formation). Suramin sodium is able to increase, as a function of the dose in the range 0.1–30 µg/ml, the number of antibody-forming cells (Table 1).

TABLE 1

Effect of suramin sodium on antibody synthesis in vitro

Antibody-secreting cells/culture as a function of the dose (µg/ml)

| Substance | 0 | 0.1 | 0.3 | 1 | 3 | 10 | 30 |
|---|---|---|---|---|---|---|---|
| Suramin sodium | 60 | 195 | 960 | 890 | 1125 | 1270 | 2155 |

Increase in the primary humoral immunity in vivo

NMRI mice were immunized subcutaneously (s.c.) with a suboptimal antigen dose (1 µg/animal). When the antigenic stimulation is suboptimal, only a small number of lymphocytes of the animals are stimulated to synthesize antibodies. The additional treatment of the animals with the compound according to the invention is able to increase significantly, either on single or on repeated administration of 3–30 mg/kg subcutaneously, the antibody titre in the serum of the animals. The antibody determination is carried out by indirect haemagglutination on day 10. The effect of the treatment is expressed by the geometric mean of $\log_2$ titre.

Increase in the non-specific, mitogen-induced stimulation of mouse spleen lymphocytes Separated spleen cells of naive, untreated Balb/c mice were subjected to non-specific stimulation with T-lymphocyte mitogen PHA (10 µg/ml) and B-lymphocyte mitogen LPS (50 µg/ml). After culturing for 48 hours, $^3$H-thymidine was added to the cultures which, after a further 16 hours, were harvested. The incorporation of radioactive thymidine into the newly synthesized DNA is regarded as a measure of the lymphocyte proliferation which has taken place. The results show a marked increase in proliferation in the dose range 1–100 µg/ml (Tab. 2).

TABLE 2

Effect of suramin sodium on the non-specific mitogen stimulation of mouse spleen lymphocytes

| | Dose (µg/ml) | | | | |
|---|---|---|---|---|---|
| | 1 | 3 | 10 | 30 | 100 |
| | $^3$H—Thymidine incorporation (% of control) | | | | |
| 0 | 70 | 90 | 70 | 120 | 70 |
| PHA | 140 | 140 | 140 | 200 | 230 |
| LPS | 130 | 140 | 140 | 220 | 160 |

The following groups of patients can be successfully treated with suramin sodium, for example:

Patients suffering from infection-related (virus, bacteria, fungi) or age-related or tumor-induced immune deficiencies or those caused by cytostatics. In addition, post-operative and post-traumatic damage to immunological resistance occurs. The treatment of patients with acquired immune deficiencies of these types is still unsatisfactory. All these patients require medication which support or normalize the body's own defenses. This can be achieved, surprisingly, with suramin sodium.

The present invention includes pharmaceutical preparations which in addition to non-toxic, inert pharmaceutically suitable excipients contain suramin sodium, or which consist of suramin sodium, and processes for the production of these preparations.

The present invention also includes pharmaceutical preparations of suramin sodium in dosage units. This means that the preparations are in the form of individual parts, for example tablets, coated tablets, capsules, pills, suppositories and ampules, of which the content of active compound corresponds to a fraction or a multiple of an individual dose. The dosage units can contain, for example, 1, 2, 3 or 4 individual doses or ½, ⅓ or ¼ of an individual dose. An individual dose preferably contains the amount of active compound which is given in one administration and which usually corresponds to a whole, a half or a third or a quarter of a daily dose.

By non-toxic, inert pharmaceutically suitable excipients there are to be understood solid, semisolid or liquid diluents, fillers and formulation auxiliaries of all kinds.

Tablets, coated tablets, capsules, pills, granules, suppositories, solutions, suspensions and emulsions, pastes, ointments, gels, creams, lotions, powders and sprays may be mentioned as preferred pharmaceutical preparations.

Tablets, coated tablets, capsules, pills and granules can contain suramin sodium alongside the customary excipients such as (a) fillers and extenders, for example starches, lactose, sucrose, glucose, mannitol and silica, (b) binders, for example carboxymethylcellulose, alginates, gelatine and polyvinylpyrrolidone, (c) humectants, for example glycerol, (d) disintegrants, for example agar-agar, calcium carbonate and sodium bicarbonate, (e) solution retarders, for example paraffin and (f) absorption accelerators, for example quaternary ammonium compounds, (g) wetting agents, for example cetyl alcohol or glycerol monostearate, (h) adsorbents, for example kaolin and bentonite and (i) lubricants, for example talc, calcium and magnesium stearate and solid polyethylene glycols, or mixtures of the substances listed under (a) to (i).

The tablets, coated tablets, capsules, pills and granules can be provided with the customary coatings and shells, optionally containing opacifying agents, and can also be of such composition that they release the suramin sodium only, or preferentially, in a certain part of the intestinal tract, optionally in a delayed manner, examples of embedding compositions which can be used being polymeric substances and waxes.

Suramin sodium, optionally together with one or more of the abovementioned excipients, can also be in a microencapsulated form.

Suppositories can contain, in addition to the active compound or compounds, the customary water-soluble or water-insoluble excipients, for example polyethylene glycols, fats, for example, cacao fat, and higher esters (for example $C_{14}$ alchol with $C_{16}$ fatty acid), or mixtures of these substances.

Powders and sprays can contain the customary excipients in addition to suramin sodium, for example lactose, talc, silica, aluminium hydroxide, calcium silicate and polyamide powders, or mixtures of these substances. Sprays can additionally contain the customary propellants, for example chlorofluorohydrocarbons.

Solutions and emulsions can contain the customary excipients in addition to suramin sodium, such as solvents, solubilizing agents and emulsifiers, for example water, ethyl alcohol, isopropyl alcohol, ethyl carbonate, ethyl acetate, benzyl alcohol, benzyl benzoate, propylene glycol, 1,3-butylene glycol, dimethylformamide, oils, especially cottonseed oil, groundnut oil, corn germ oil, olive oil, castor oil and sesame oil, glycerol, glycerol-formal, tetrahydrofurfuryl alcohol, polyethylene glycols and fatty acid esters of sorbitan, or mixtures of these substances.

For parenteral administration, the solutions and emulsions can also be in a sterile form which is isotonic with blood.

Suspensions can contain the customary excipients in addition to suramin sodium, such as liquid diluents, for example water, ethyl alchol, propylene glycol, suspending agents, for example ethoxylated isostearyl alcohols, polyoxyethylene sorbitol and sorbitan esters, microcrystalline cellulose, aluminum metahyroxide, bentonite, agar-agar and tragacanth, or mixtures of these substances.

The formulation forms mentioned can also contain dyestuffs, preservatives and additives which improve the odour and flavour, for example peppermint oil and eucalyptus oil, and sweeteners, for example saccharin.

Suramin sodium should preferably be present in the abovementioned pharmaceutical preparations in a concentration of about 0.1 to 99.5, preferably from about 0.5 to 95, % by weight of the total mixture.

The abovementioned pharmaceutical preparations can also contain other pharmaceutical active compounds in addition to suramin sodium.

The abovementioned pharmaceutical preparations are manufactured in the usual manner according to known methods, for example by mixing the active compound with the excipient or excipients.

The present invention also includes the use of suramin sodium and of pharmaceutical preparations which contain the active compound in human and veterinary medicine for the prevention, amelioration and/or cure of the abovementioned illnesses.

The active compound or the pharmaceutical preparations can be administered locally, orally, parenterally, intraperitoneally and/or rectally, preferably parenterally, in particular intravenously.

In general, it has proved advantageous both in human medicine and in veterinary medicine to administer suramin sodium in total amounts of about 1.0 to 300, preferably 3.0 to 30, mg/kg, in particular 2.5 to 25 mg/kg, of body weight every 24 hours, optionally in the form of several individual administrations, in order to obtain the desired results.

However, it can be necessary to deviate from the dosages mentioned and, in particular, to do so as a function of the nature and body weight of the subject to be treated, the nature and the severity of the illness, the nature of the preparation and of the administration of the medicine, and the time or interval over which the administration takes place. Thus, it can suffice in some cases to manage with less than the abovementioned amount of active compound, while in other cases the abovementioned amount of active compound must be exceeded.

The particular required optimum dosage and the type of administration of the active compounds can easily be decided by anyone skilled in the art on the basis of his expert knowledge.

It will be understood that the specification and examples are illustrative but not limitative of the present invention and that other embodiments within the spirit and scope of the invention will suggest themselves to those skilled in the art.

We claim:

1. A method of stimulating the immune response of a patient which comprises administering to a patient in need thereof an immunostimulating effective amount of 8,8'-[carbonylbis[imino-3,1-phenylenecarbonylimino(4-methyl-3,1-phenylene)carbonylimino]]bis 1,3,5-naphthalenetrisulphonic acid hexasodium salt.

* * * * *